US010245083B1

(12) United States Patent
Shapiro

(10) Patent No.: US 10,245,083 B1
(45) Date of Patent: Apr. 2, 2019

(54) METHOD AND DEVICE FOR MINIMIZING THE RISK OF FUTURE HIP FRACTURES

(71) Applicant: Michael R Shapiro, Bell Canyon, CA (US)

(72) Inventor: Michael R Shapiro, Bell Canyon, CA (US)

(*) Notice: Subject to any disclaimer, the term of this patent is extended or adjusted under 35 U.S.C. 154(b) by 0 days.

(21) Appl. No.: 15/859,649

(22) Filed: Dec. 31, 2017

(51) Int. Cl.
*A61B 17/74* (2006.01)

(52) U.S. Cl.
CPC .................. *A61B 17/744* (2013.01)

(58) Field of Classification Search
CPC ...... A61B 17/744; A61B 17/74; A61B 17/746
USPC ............. 606/62, 64; 623/22.11, 20.35, 20.36
See application file for complete search history.

(56) References Cited

U.S. PATENT DOCUMENTS

| | | | | |
|---|---|---|---|---|
| 6,447,514 B1* | 9/2002 | Stalcup | ................. | A61B 17/164 606/63 |
| 7,854,767 B2* | 12/2010 | May | ..................... | A61B 17/744 623/18.11 |
| 7,918,853 B2* | 4/2011 | Watanabe | ............ | A61B 17/164 606/62 |
| 2004/0049192 A1* | 3/2004 | Shimizu | ............. | A61B 17/7098 606/62 |
| 2011/0295255 A1* | 12/2011 | Roberts | ................ | A61B 17/744 606/64 |
| 2012/0197254 A1* | 8/2012 | Wolfe | ................ | A61B 17/1717 606/62 |

* cited by examiner

*Primary Examiner* — Pedro Philogene
*Assistant Examiner* — David C Comstock
(74) *Attorney, Agent, or Firm* — Brooks Kushman P.C.

(57) ABSTRACT

Two implant devices cooperate to form a single reinforcement device for minimizing the risk of future hip fractures in the vulnerable intertrochanteric and adjacent femoral neck regions of a patient identified as being at significant risk for hip fracture. The two implant devices are sequentially inserted through the same incision and each has a respective head portion, a respectively upwardly or downwardly curved intermediate portion preferably having a generally constant rectangular cross section, and a tapered tail portion, with the head portion of the first implant device having a suitably shaped and positioned opening adapted to receive the constant cross section portion of the second device, and with an enlarged head portion of the second implant device adapted to maintain the second device at a desired orientation relative to the first device and to constrain the second device from excessive insertion relative to the first device after the two devices have been sequentially inserted through the single incision.

9 Claims, 8 Drawing Sheets

US 10,245,083 B1

METHOD AND DEVICE FOR MINIMIZING THE RISK OF FUTURE HIP FRACTURES

FIELD OF THE INVENTION

The present invention relates generally to orthopedic medicine, and more particularly to surgical procedures and devices for managing and preventing hip fractures.

BACKGROUND

The enlarged intertrochanteric region at the upper end of the human thigh bone (in latin "femur") connects the upper portion of the generally vertical femoral shaft with a generally horizontal femoral neck having a somewhat smaller cross section, which in turn terminates in an enlarged spherical femoral head which is adapted for rotation in a respective spherical socket (in latin "acetabulum") on each side of the human pelvis. The intertrochanteric region is defined by two enlarged prominences—a greater trochanter having a relatively flat, broad surface on the outside of the femur and a lesser trochanter having a relatively short conical surface on the inside of the femur—to which are attached various muscles and ligaments, including those which connect the thigh to the pelvis.

The upper portion of the femur and in particular its intertrochanteric and adjacent neck regions are critical paths for weight bearing through the skeletal system and are therefore subject to comparatively high levels of dynamic stress, nail pathological strain, physiological strain, and trauma. In particular, this region is prone to fractures due to high velocity trauma in the young and trivial trauma in the elderly. The fractures in this area are called intertrochanteric fractures (in common parlance, "hip fractures") and are classified as per the pattern of the fracture geometry. After such a fracture, the resultant bone tissue fragments are notorious for re-uniting in varying, and sometimes problematic angles relative to each other and to the intramedullary portion of the femur. Therefore, a hip fracture typically requires early surgical reduction and fixation followed by prompt commencement of mobilization and weight bearing in order to facilitate enhanced recovery.

Particularly in the elderly, osteoporosis (reduced density and impaired structural integrity) of the bone tissue in this area further increases the risk of complex fractures and problematic functional recovery. The World Health Organization Fracture Prediction Tool, or WHO FRAX for short, is a recognized and accepted tool for predicting susceptibility to hip fractures, and can be downloaded on the internet. Accordingly, recognized experts such as The American Academy of Orthopedic Surgeons (AAOS) have officially encouraged orthopedists to become involved in "bone fragility" screening to create clinics that use statistical screening and bone density studies to identify patients that are at significant risk for hip fracture and that would benefit from prophylactic treatment with prolia or boniva or other appropriate medications to prevent further bone loss.

Repair and reinforcement of complex fractures of the femoral shaft using elongated intramedullary nails has been a standard surgical procedure since World War I, and threaded nails (screws) have been used both to facilitate realignment of the separated intertrochanteric bone fragments and to apply tension to hold them in position. More recently, combinations of intramedullary nails and intertrochanteric screws have been commercially available for repairing existing hip fractures in the intertrochanteric and adjacent femoral neck regions by realigning the bone fragments and applying tension to promote healing. Although in theory such known hip fracture repair devices could be used prophylactically to provide protection from future fractures in an intact femur, the known devices and surgical procedures are relatively complex, invasive, and time consuming, and any such prophylactic use is neither medically advisable nor cost effective.

SUMMARY OF THE INVENTION

The present invention has two related aspects: (1) a relatively simple surgical procedure that requires only one incision for minimizing the risk of future hip fractures in the vulnerable intertrochanteric and adjacent femoral neck regions of patients identified as being at significant risk, and (2) a novel two-piece implant device suitable for use in such procedures.

In a presently preferred implementation of the surgical procedure, a single relatively small incision (approximately one inch long) is made in the skin and underlying soft tissue in the vicinity of the lateral (outer) surface of the femur adjacent the Intertrochanteric region, and otherwise conventional canulated reamers and rasps are used (preferably with fluoroscopic guidance) to open a pair of intersecting curved passageways from the single incision site and through the Intertrochanteric region, with one of the curved passageways further extending downwardly into the femoral body for receiving an intramedullary component of a two piece reinforcing device and the other curved passageway further extending upwardly into the femoral neck for receiving a femoral neck component of the device.

A first curved reinforcement implant device is inserted into a corresponding first curved passageway and a second curved reinforcement implant device is then inserted into a corresponding second curved passageway, with the outer end of at least one of the two curved implant devices preferably mechanically secured within the incision region to an adjacent outer end of the other implant device, whereupon the single incision may be closed and the internal living tissue surrounding the two implant devices forming over time an intimate bond with their outer surfaces, thereby permanently securing the two implanted devices in their respective intended positions both relative to each other and to the surrounding bone.

In a presently preferred implementation of the two implant devices which cooperate to form a single reinforcement device, each implant device has a respective head portion, a curved intermediate portion having a generally constant rectangular cross section, and a tapered tail portion, with the head portion of the first implant device having a suitable shaped and positioned opening adapted to receive the constant cross section portion of the second device, and with an enlarged head portion of the second implant device adapted to maintain the second device at a desired orientation relative to the first device and to constrain the second device from excessive insertion relative to the first device.

In one embodiment, the first implant device is configured to inserted upwardly into the femoral neck before the second implant device is inserted downwardly through the head of the first device into the femoral body. In an alternative embodiment, the first implant device is configured to be inserted downwardly into the femoral body before the second implant device is inserted upwardly through the head of the first device into the femoral neck.

If the femoral neck component is positioned before the intramedullary component, any downward weightbearing force on the hip will act to maintain the two components in fixed intimate contact. However, in either configuration, a locking screw is preferably placed through the enlarged head portion of the second component and into an adjacent portion of the first component, thereby providing greater strength and rigidity to the assembled device during the healing process.

In other embodiments, at least one of the implant devices may be formed of at least two parts that are successively placed adjacent to each other in the same respective curved passageway and subsequently secured together to function as a single implant device having an open area between those two parts into which human tissue may grow.

In accordance with yet another aspect of the present invention, the downwardly extending lower end of the prophylactic femoral shaft component is preferably provided with a suitably shaped and dimensioned end termination configuration to cooperate with a complementary shaped and dimensioned upper end of an otherwise conventional femoral retrograde intramedullary fixation nail, in the unlikely event that the patient in whom the upper femur reinforcement device has been placed subsequently experiences a fracture in the lower femur.

DRAWINGS

Figure 8:
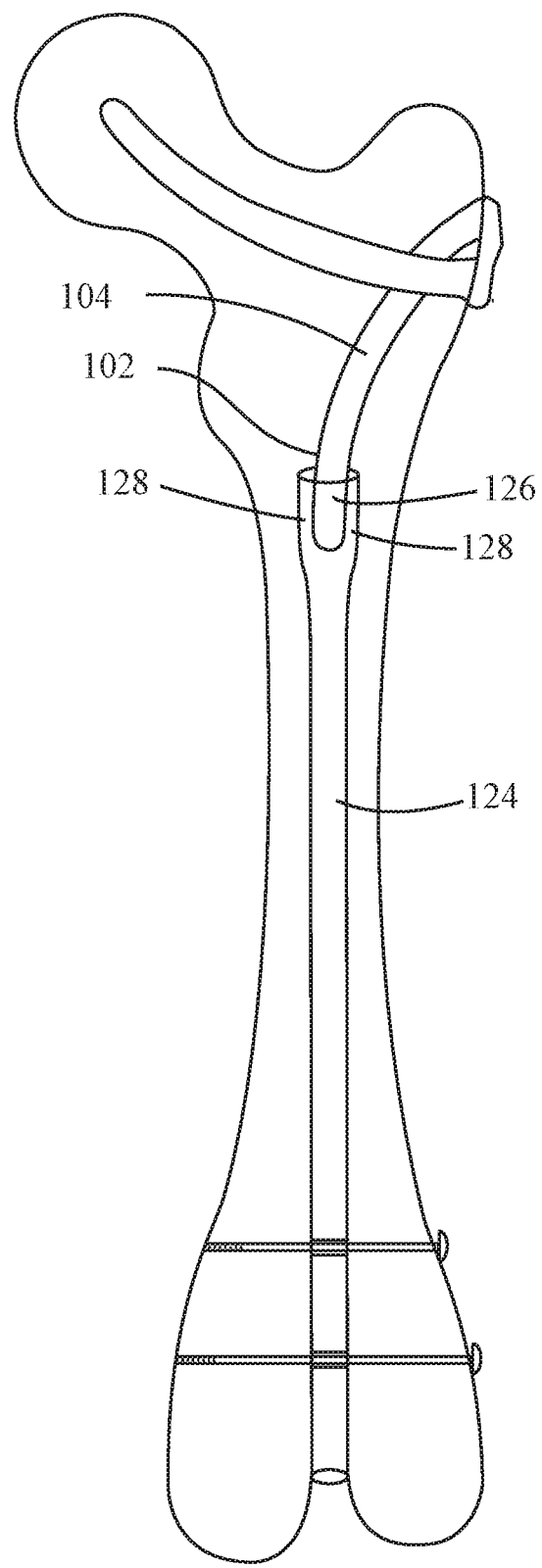

FIG. 8 shows how the downwardly extending lower end of the femoral shaft component can be provided with a suitably shaped and dimensioned end termination configuration to cooperate with a complementary shaped and dimensioned upper end of an otherwise conventional femoral retrograde intramedullary fixation nail, thereby obviating any need to modify or remove a previously installed upper femoral reinforcement device in the unlikely event that a femoral retrograde intramedullary fixation nail must be inserted upwardly into the region occupied by the previously installed device at the upper end of the femoral shaft.

DETAILED DESCRIPTION OF PRESENTLY PREFERRED EMBODIMENTS

Figure 1:
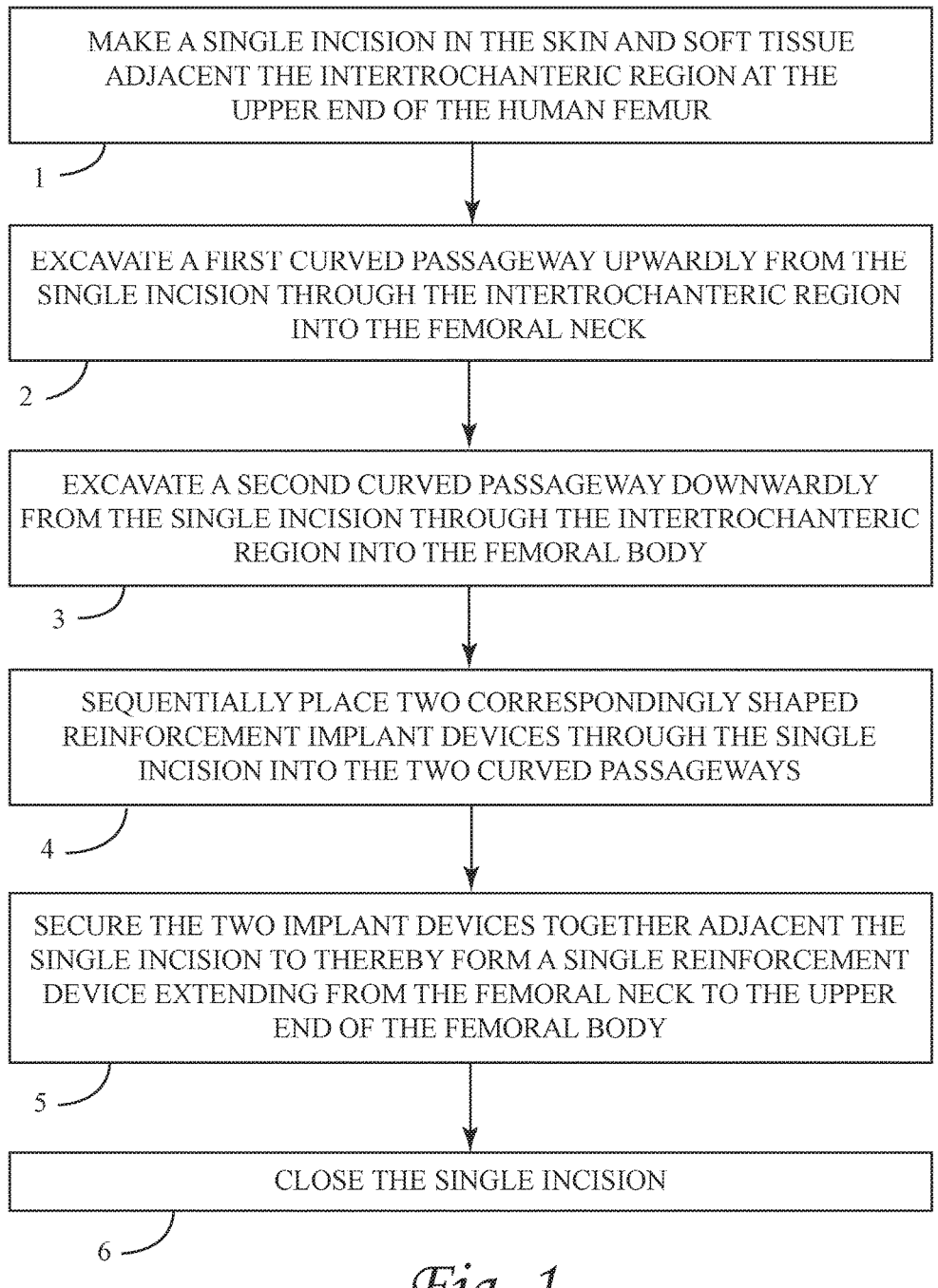
FIG. 1 is a flowchart showing the steps of an exemplary surgical procedure for providing a patient with protection from hip fractures.

A preferred surgical procedure for providing an at-risk patient with protection from hip fractures is outlined in FIG. 1. Unlike conventional hip fracture repair surgery, only a single incision is required, typically in the skin and soft tissue adjacent the intertrochanteric region of the femur (see step 1 of FIG. 1, also FIG. 2 and FIG. 6), preferably with only local anesthesia and light sedation such as is typically used for a colonoscopy.

Canulated reamers and rasps are then used (preferably with fluoroscopic guidance) to open first (step 2) and second (step 3) intersecting curved passageways from the single incision site with the first passageway extending downwardly into the femoral body for receiving an intramedullary component of the reinforcement device and the second passageway extending upwardly through the Intertrochanteric region and into the femoral neck for receiving a femoral neck component of the reinforcement device (step 4).

The intramedullary and femoral neck components are then secured together (step 5) and the single incision is closed (step 6).

Figure 2:
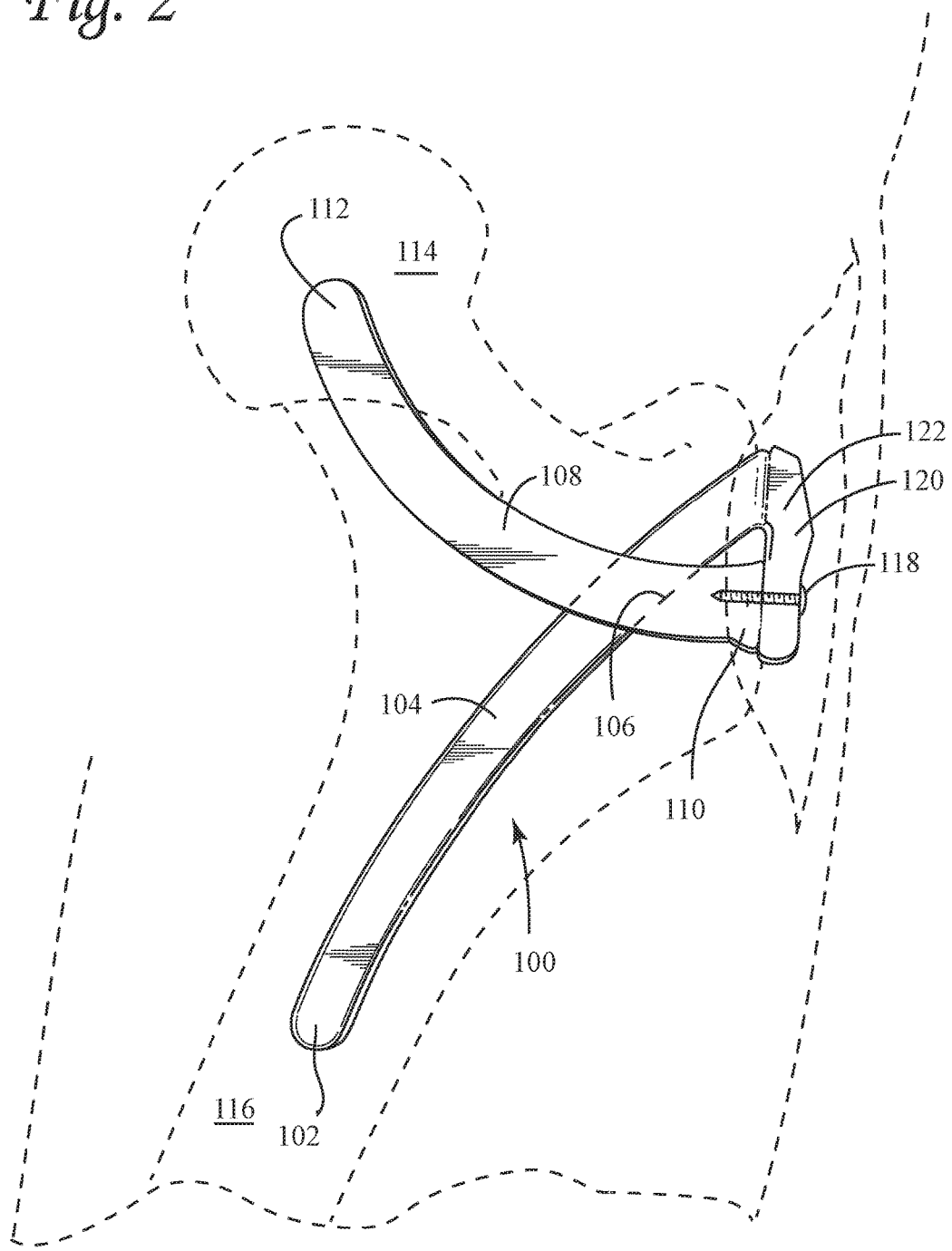
FIG. 2 is a schematic lateral view of the upper thigh of a human patient including the skin and bone surrounding the upper end of a human femur into which a two-piece femoral reinforcement device comprising an upwardly curved femoral neck portion and a downwardly curved femoral body portion has been inserted through a single incision.
Figure 3:
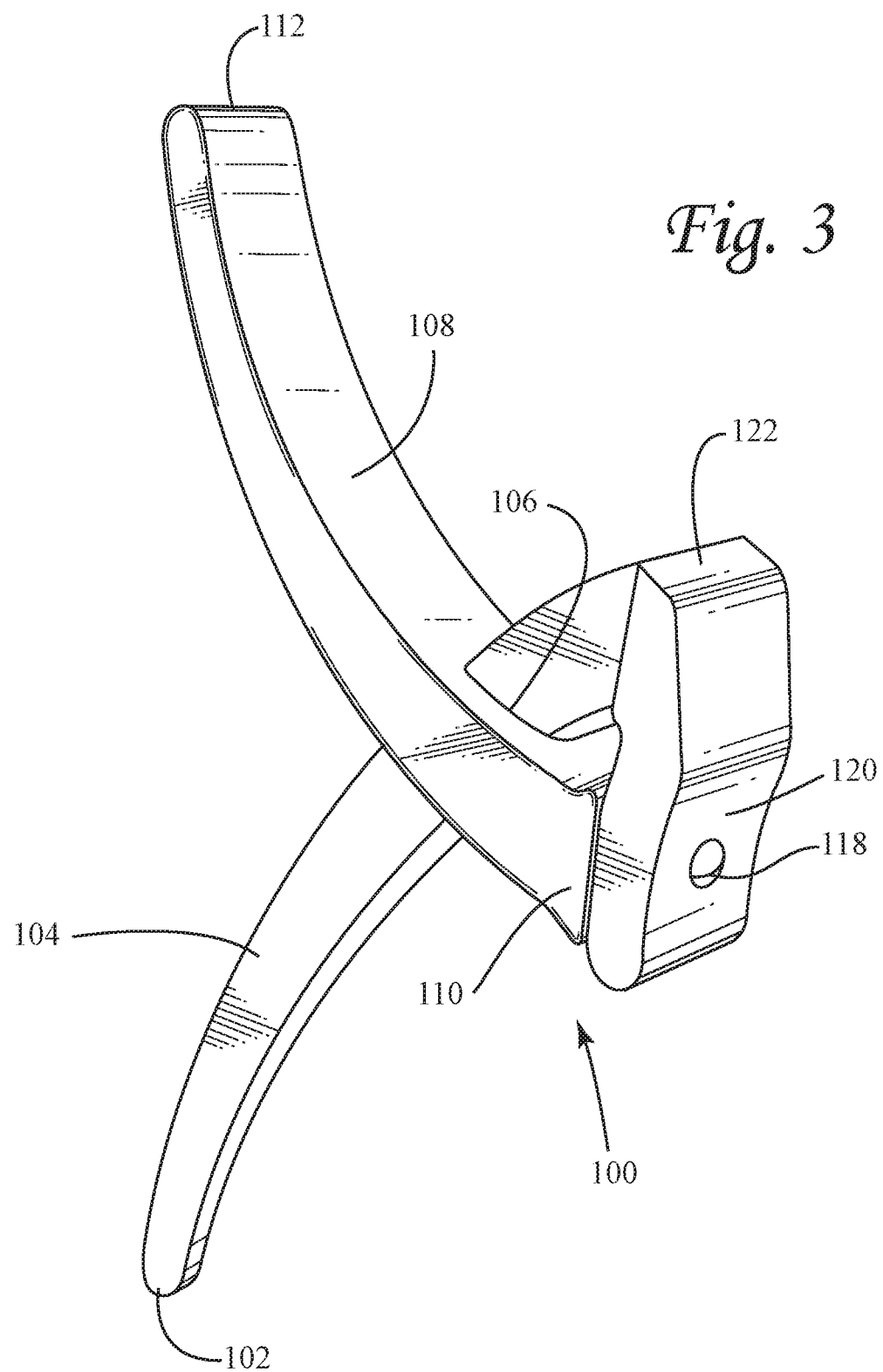
FIG. 3 is an isometric view of the assembled femoral reinforcement device of FIG. 2.
Figure 4:
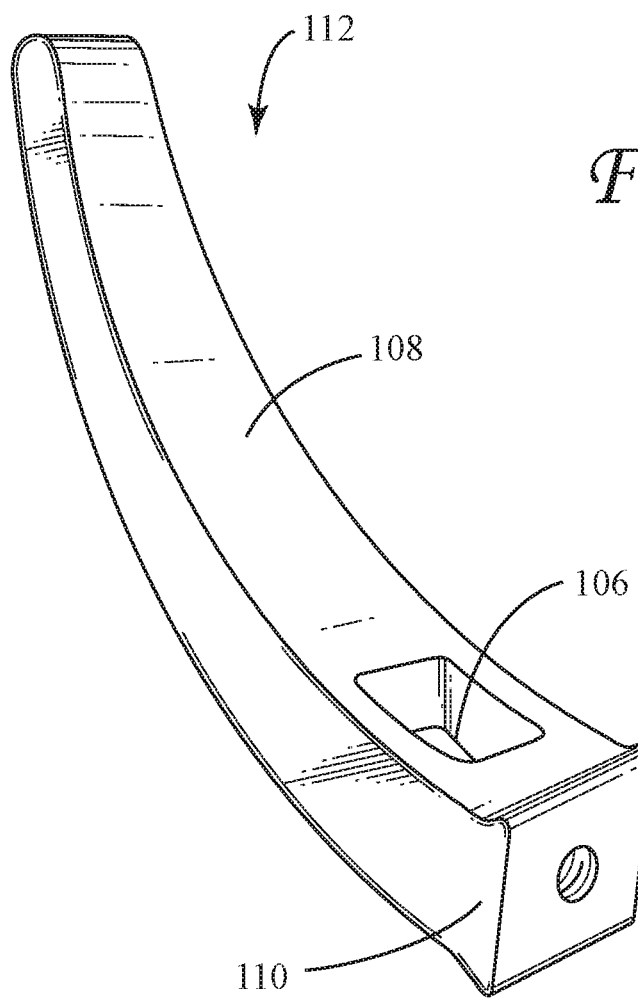
FIG. 4 is an isometric view of the upwardly curved femoral neck component of the device of FIG. 2 which more clearly shows the rectangular opening into which may be inserted the corresponding rectangular profile of the downwardly curved femoral shaft (intramedullary) component of the device of FIG. 2.
Figure 5:
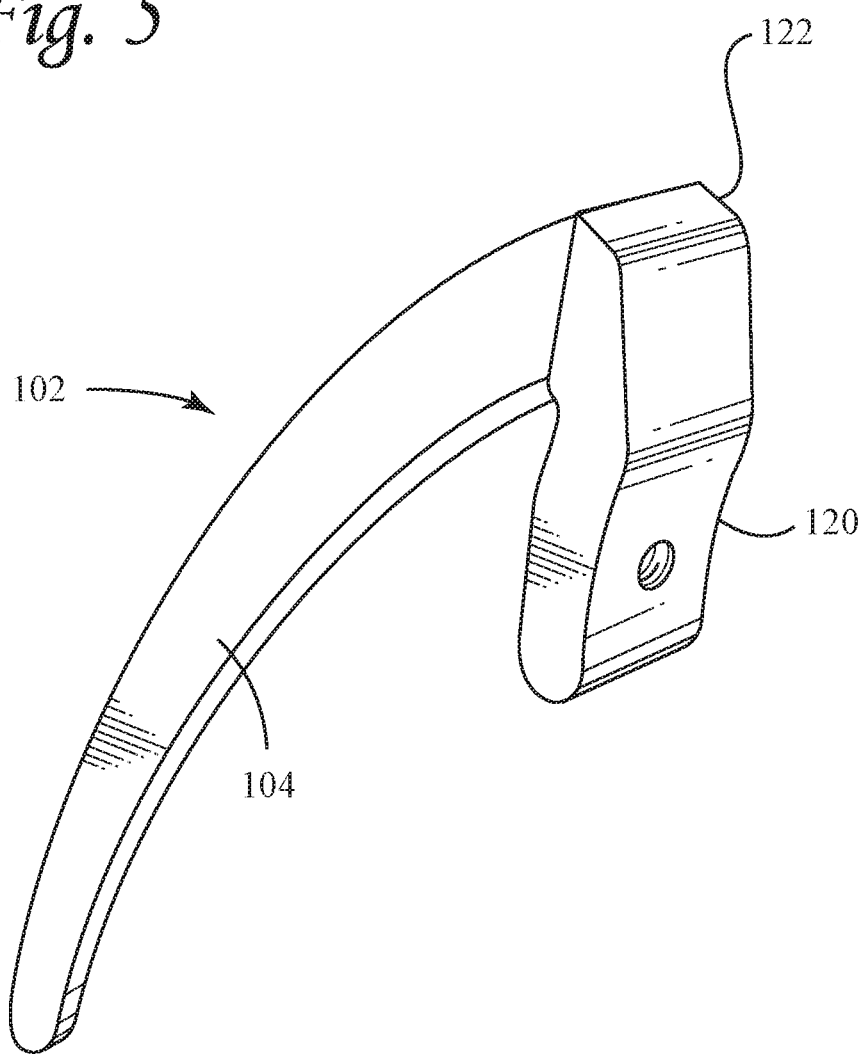
FIG. 5 is an isometric view of the downwardly curved femoral shaft component of the device of FIG. 2 which more clearly shows how the downwardly curved body portion has a relatively narrow rectangular cross section to facilitate its insertion into the similarly dimensioned rectangular opening shown in FIG. 4 and the enlarged head portion which maintains the two components in intimate contact.

In one presently preferred embodiment of the reinforcement device 100 as shown in FIG. 2 and FIG. 3, the intramedullary component 102 has a downwardly curved shaft portion 104 with a non-circular (preferably rectangular) profile and is inserted through a corresponding shaped opening 106 in the upwardly extending curved shaft portion 108 below the head 110 of the previously inserted femoral neck component 112 (see also FIG. 4 and FIG. 5), whereby, as best seen in FIG. 2, the two components 102,112 are secured together to form a single reinforcement device 100 extending from the femoral neck 114 to the upper end of the femoral body 116. An optional locking screw 118 may be inserted through a lateral flange 120 on the offset head 122 of the intramedullary component 102 and into the enlarged head 110 of the femoral neck component 112, thereby providing greater strength and rigidity to the assembled device during the healing process, and the incision is then closed.

Figure 6:
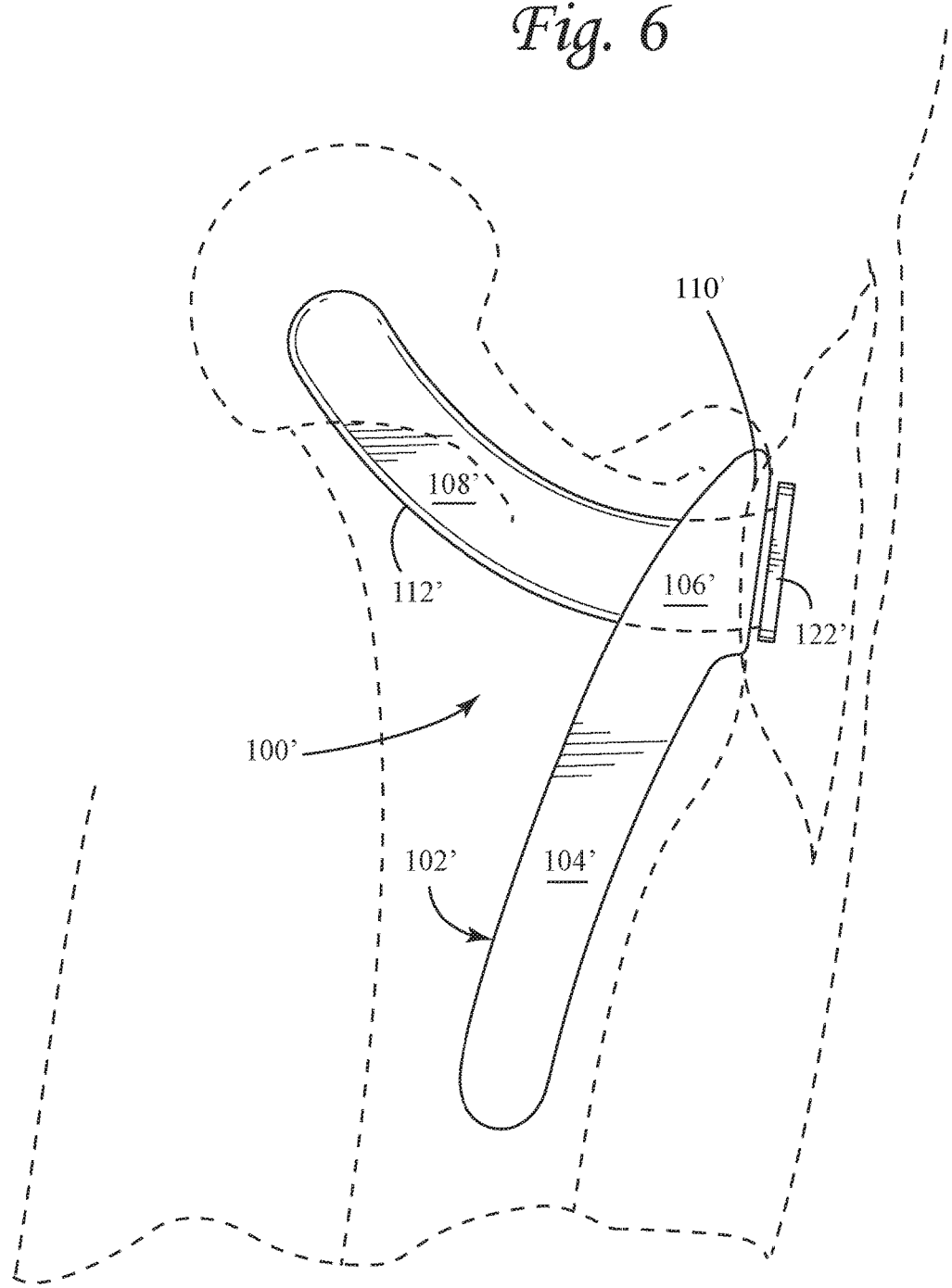
FIG. 6 is a schematic lateral cross section through the hip region of a human patient showing the skin and bone surrounding the upper end of a human femur, with an upwardly curved femoral neck portion of an alternative embodiment of a femoral reinforcement device inserted through the head of a previously inserted downwardly curved femoral body portion of that device.

FIG. 6 shows an alternate embodiment of the reinforcement device 100' in which the downwardly curved shaft 104' of a modified intramedullary component 102' is inserted first and is provided with a suitably shaped rectangular opening 106' below enlarged head 110', though which the modified rectangular shaft 108' of a modified upwardly curved femoral neck component 112' with modified head 122' may be sequentially inserted through opening 106'.

Figure 7:
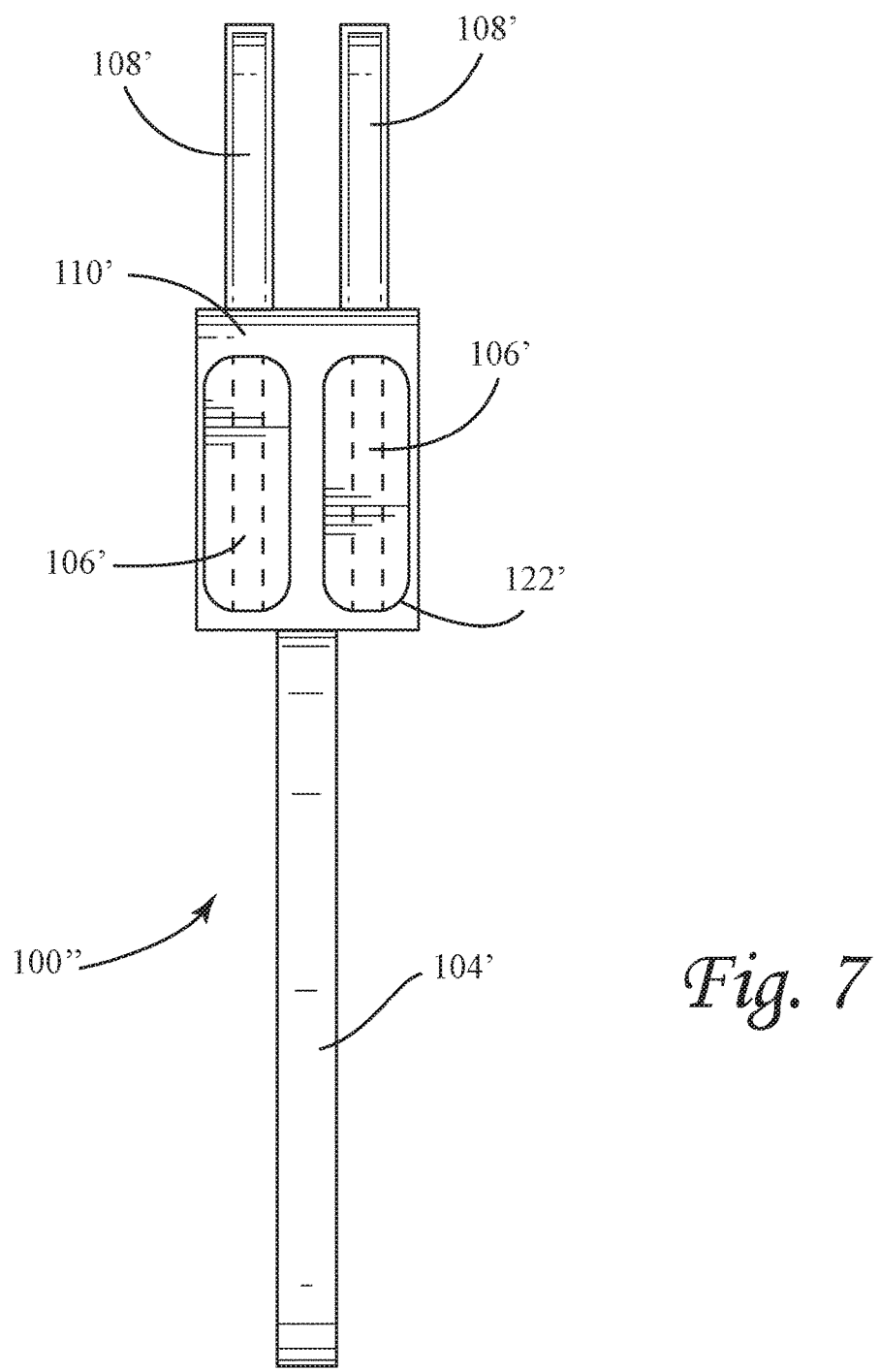
FIG. 7 shows another alternative embodiment of a femoral reinforcement device similar to the embodiments of FIG. 2 and FIG. 6, in which one of the curved portions is formed of two similarly shaped parts that are adapted to be inserted sequentially into two respective slots extending through the head of the other curved portion into and the same curved passageway.

FIG. 7 is a front view of a variation of the two piece reinforcement devices of FIG. 1 and FIG. 6, which shows how one of the relatively thick curved components of a two piece reinforcement device (for example, upwardly curved femoral neck component 108' of FIG. 6) may be replaced with two or more adjacent side by side components 108" which are similarly shaped but thinner, and which do not necessarily all have identical physical characteristics to each other, thereby permitting sequential insertion of the second components 108" through the head 110" of the first component and facilitating alignment of the fully assembled reinforcement device 100″ with respect to the two surgically opened upwardly and downwardly curved passageways.

FIG. 8 is a front view of the entire human femur in which a modified version of the two piece reinforcement device 100 of FIG. 2 has been extended downwardly by a modified femoral retrograde intramedullary fixation nail 124. In particular, the downwardly extending lower end 102 of the femoral shaft component 104 can be provided with a male termination portion 126 that cooperates with a complementary shaped and dimensioned female termination 128 on the upper end of an otherwise conventional femoral retrograde intramedullary fixation nail 124, thereby transferring the patient's weight from the upper femoral reinforcement device 104″ to the lower end of the femur through lower portion of the femur that is now reinforced by the retrograde intramedullary fixation nail 124 and obviating any need to remove the upper femoral reinforcement device 104″ in the event that at some future time, a longer femoral retrograde intramedullary fixation nail must be inserted upwardly into the region occupied by a previously inserted reinforcement device 100″ at the upper end of the femoral shaft. Although the illustrated fixation nail 124 is not provided with any specific mechanical holding means other than the opposing generally cone shaped male and female components 126 and 128, those skilled in the art will recognize that other coupling means could be substituted for the simple illustrated configuration. For example, the opposing ends could be provided with complementary threaded or rotationally locked portions Although the described embodiments of the two coupled implant device components have certain specific structural attributes, it will be understood that other functionally equivalent structure may be substituted without departing from the spirit of the claimed invention. For example, a square or triangular or oval cross section and opening may be substituted for the preferred rectangular cross section and opening and may still provide sufficient strength and stability without adding excessive cost or complexity. As another example, although each of the described components is shown as being solid and homogenous and biologically inert, they could be hollow and/or coated with biologically active compounds.

Similarly, although the described embodiments of the invention use materials and processes that are recognized today as medically safe and effective, rather than technology that is currently unknown to the medical profession or is considered as having unknown risks or as not being cost effective, the claimed invention should not necessarily be so limited. For example, any required incisions or excavations could perhaps be made using lasers and/or robots and/or the required implant devices could perhaps be custom made in real time from a biologically inert material using computerized 3D printing with shapes and dimensions derived from realtime radiological scans taken during the surgical procedure.

The invention claimed is:

1. A femoral reinforcement prophylactic device adapted to be placed into a surgically excavated upper portion of a human femur rotatably connected to one side of the human pelvis, an upper portion of the femur including an integrally formed inwardly extending neck terminating in an integrally formed generally ball shaped head constrained within a corresponding outwardly extending socket on the pelvis, the femoral reinforcement device comprising at least two separate and distinctly shaped implant components: a downwardly curved implant component adapted to be inserted downwardly and inwardly into a first correspondingly shaped excavation extending downwardly from the intertrochanteric region and into an intramedullary portion of the femur, said downwardly curved implant component having a first non-circular cross section for restricting rotation relative to the correspondingly shaped excavated portions of the femur into which the downward curved implant component is being inserted; and an upwardly curved implant component adapted to be inserted upwardly and inwardly into a correspondingly shaped excavation extending upwardly from the intertrochanteric region through the neck and into the ball-shaped head of the femur, said upwardly curved implant component having a second non-circular profile for restricting rotation of the second implant component relative to the correspondingly shaped excavated portions of the intertrochanteric, neck and head portions of the femur into which the upwardly curved implant component is being inserted, wherein the upper end of the downwardly curved implant component and the lower end of the upwardly curved implant component comprise respective integrally formed mating portions for securing the two implant components from rotation relative each other once both implant components have been inserted into the intertrochanteric region, and wherein the downwardly curved implant component further comprises means for coupling the downwardly curved implant component to an upper end of a femoral retrograde intramedullary fixation nail that is subsequently inserted upwardly into the intertrochanteric region from the lower end of the human femur.

2. The device of claim 1, wherein the mating portion of the downwardly curved implant component is provided with an opening that is configured and dimensioned to receive the mating portion of the upwardly curved implant component.

3. The device of claim 1, wherein the mating portion of the upwardly curved implant component is provided with an opening that is configured and dimensioned to receive the mating portion of the downwardly curved implant component.

4. A surgical procedure for reducing the risk of fracture of the neck and head portions of the human femur in a patient having an intact femur with native neck and head portions at its upper end, but who has been determined to have a statistically significant "bone fragility" score indicative of a high risk of future hip fracture, comprising the steps:

a. making a single incision in the skin and underlying internal tissue in the vicinity of the lateral outer surface of the femur adjacent the intertrochanteric region, to thereby form an enlarged space between the skin and the femur;

b. surgically opening two curved passageways each having a respective gradually tapered non-circular cross section from the outer lateral surface of the femur adjacent the enlarged space and into the intertrochanteric region of the femur, including a downwardly extending curved passageway having a respective gradually tapered non-circular cross section through the intertrochanteric region and into the femoral body and an upwardly extending curved passageway having a respective gradually tapered non-circular cross section through the intertrochanteric region and into the femoral neck and head;

c. inserting a first curved reinforcement implant device though the single incision and into a respective first of the two curved passageways through the intertrochanteric region and into the corresponding femoral head or femoral body;

d. inserting a second curved reinforcement implant device though the same single incision and a respective opening in the first curved implant device, into a respective second of the two curved passageways through the intertrochanteric region and into the corresponding femoral body or femoral head, and e. closing the single incision, whereupon living tissue surrounding the two curved reinforcement implant devices forms over time an intimate bond with their respective outer surfaces, thereby permanently securing the two implanted devices in their respective intended positions both relative to each other and to the femoral body, wherein the shape and orientation of each of the two implant devices generally corresponds to the shape and orientation of its respective curved passageway and has a respective cross section slightly smaller than that of its respective passageway to thereby facilitate insertion without excessive force and avoidance of excessive stress on the femoral regions through which it extends.

5. The surgical procedure of claim 4, wherein a body portion of the second implant device is inserted into its respective passageway through a corresponding opening in a neck portion of the previously inserted first device, with an enlarged head portion of the second implant device in contact with the neck portion of the first implant device, thereby securing the first implant device against unintentional extraction.

6. The surgical procedure of claim 5, wherein the body portion of the second implant device has a non-circular external profile corresponding to the interior profile of the opening in the neck of the first implant device, thereby securing the second implant device against unintentional rotation relative to the first implant device.

7. The surgical procedure of claim 6, wherein the first implant device extends upwardly into the femoral neck and head, and the second implant device extends downwardly into the femoral body.

8. The surgical procedure of claim 6, wherein the first implant device extends downwardly into the femoral body and the second implant device extends upwardly into the femoral neck and head.

9. The surgical procedure of claim 5, wherein a lower end of the downwardly curved reinforcement implant device further comprises means for coupling the downwardly curved implant device to an upper end of a femoral retrograde intramedullary fixation nail that is subsequently inserted upwardly from the lower end of the human femur.

* * * * *